US012778966B2

(12) United States Patent
Li et al.

(10) Patent No.: US 12,778,966 B2
(45) Date of Patent: Nov. 3, 2026

(54) COBALT-CONTAINING ACIDIC AMINO ACID COMPLEX AND ITS USE FOR TREATING CANCER

(71) Applicant: AMELIO BIOMEDICAL CO., LTD., Taipei City (TW)

(72) Inventors: I-Chen Li, New Taipei City (TW); Chi-Jung Chen, New Taipei City (TW)

(73) Assignee: AMELIO BIOMEDICAL CO., LTD., Taipei City (TW)

( * ) Notice: Subject to any disclaimer, the term of this patent is extended or adjusted under 35 U.S.C. 154(b) by 310 days.

(21) Appl. No.: 18/698,715

(22) PCT Filed: Sep. 30, 2022

(86) PCT No.: PCT/CN2022/123300

§ 371 (c)(1),
(2) Date: Apr. 4, 2024

(87) PCT Pub. No.: WO2023/056898

PCT Pub. Date: Apr. 13, 2023

(65) Prior Publication Data

US 2024/0398829 A1 Dec. 5, 2024

Related U.S. Application Data

(60) Provisional application No. 63/252,232, filed on Oct. 5, 2021.

(51) Int. Cl.
*A61K 31/555* (2006.01)
*A61P 35/00* (2006.01)

(52) U.S. Cl.
CPC ............ *A61K 31/555* (2013.01); *A61P 35/00* (2018.01)

(58) Field of Classification Search
CPC .............................. A61K 31/555; A61P 35/00
See application file for complete search history.

(56) References Cited

FOREIGN PATENT DOCUMENTS

| | | | |
|---|---|---|---|
| JP | 2010-90064 A | | 4/2010 |
| WO | WO 2004/035524 A1 | | 4/2004 |
| WO | WO 2004/050884 A1 | | 6/2004 |
| WO | 2008/007868 | * | 1/2008 |
| WO | WO 2008/007888 A1 | | 1/2008 |

OTHER PUBLICATIONS

Doyne et al., "Cyclic configuration of the aspartate ion in the crystal structure of zinc, cobaltous and nickelous aspartate trihydrate," Acta Cryst., Dec. 31, 1957, pp. 438-439.

Ji et al., "Synthesis and Properties of Tyrosine-cobalt Complex," Chin. J. Syn. Chem., vol. 28, No. 9, Dec. 31, 2020, pp. 806-809.

Li et al., "Study on Synthesis and Properties of Complexes of Arginine and Cobalt," Chemical Reagents, vol. 43, No. 10, Jul. 23, 2021, pp. 1348-1352.

Li et al., "Synthesis, toxicity and antitumor activity of cobalt carbonyl complexes targeting hepatocellular carcinoma," Bioorganic & Medicinal Chemistry, Elsevier, vol. 27, Aug. 23, 2019, pp. 1-11.

Zhang et al., "[Cobalt(II)L-glutamate(H2O)-H2O]∞ : a new 3D chiral metal-organic interlocking network with channels," Cryst. Eng. Comm., vol. 5, No. 5, Jan. 16, 2003, pp. 34-37.

Extended European Search Report for European Application No. 22877917.9, dated Sep. 24, 2025.

Isamil et al., "Thermal studies and mass loss inhibition for some new mixed amino acid metal complexes with their applications," Journal of Thermal Analysis and Calorimetry, vol. 125, No. 1, Apr. 9, 2016, XP035921972, pp. 289-300.

* cited by examiner

*Primary Examiner* — D Margaret M Seaman

(74) *Attorney, Agent, or Firm* — Birch, Stewart, Kolasch & Birch, LLP

(57) ABSTRACT

A cobalt-containing acidic amino acid complex and its use for treating cancer. In some embodiments, the cobalt-containing complex is represented by Formula I or II.

7 Claims, 10 Drawing Sheets

COBALT-CONTAINING ACIDIC AMINO ACID COMPLEX AND ITS USE FOR TREATING CANCER

CROSS REFERENCE TO RELATED APPLICATIONS

This application is the National Phase of PCT International Application No. PCT/CN2022/123300, filed on Sep. 30, 2022, which claims priority under 35 U.S.C. 119 (e) to U.S. Provisional Application No. 63/252,232, filed on Oct. 5, 2021, all of which are hereby expressly incorporated by reference into the present application.

FIELD OF THE INVENTION

The present invention relates to a cobalt-containing acidic amino acid complex and its use for treating cancer.

BACKGROUND OF THE INVENTION

Cancer is one of the most important health problems in the world. It is defined as the old cells growing out of control, escaping from death and developing anywhere in the body. Patients are treated with either traditional therapies such as surgery, radiation therapy, and chemotherapy or newer forms of treatment such as immunotherapy, targeted therapy, gene therapy, etc. Chemotherapy is an effective and widespread cancer treatment which uses one or more anti-cancer drugs.

Cisplatin is a Pt(II) complex and is used as a chemotherapeutic drug to treat many types of cancers. Its chemical formula is $[Pt(NH_3)_2Cl_2]$ and molar mass is 300.05 $g \cdot mol^{-1}$. It interferes cell mitosis by crosslinking with DNA and activates apoptosis when the cell fails to repair the damage DNA. Therefore, cisplatin can kill proliferating cells including cancer cells. It can also damage normal cells which divide rapidly such as bone marrow, gastrointestinal tract and hair follicles. The common side effects such as nephrotoxicity, ototoxicity, hepatotoxicity, gastrointestinal intolerance, and neurotoxicity. Due to acquired or inherent resistance, non-specific and toxic side effects, and incapability of preventing cancer recurrence, the clinical usage of cisplatin is limited (Sumit Ghosh Chemistry. 88, 102925, (2019)).

BRIEF SUMMARY OF THE INVENTION

In the present invention, it is unexpected found that a cobalt-containing complex with an acidic acid amino acid, including glutamic acid (GA, Glu) or aspartic acid (AA, Asp), is effective in inhibiting cancer cell growth. In particular, a cobalt-containing complex with an acidic acid amino acid as described herein is effective as a broad-spectrum anti-cancer agent because of its effect against various types of cancer cells.

Therefore, the present invention provides a method for treating cancer in a subject in need thereof comprising administering an effective amount of a cobalt-containing complex with an acidic acid amino acid to the subject. The present invention also provides use of a cobalt-containing complex with an acidic acid amino acid for manufacturing a medicament for treating cancer in a subject in need. Further provided is a pharmaceutical composition for use in treating cancer comprising a cobalt-containing complex with an acidic acid amino acid and a pharmaceutically acceptable carrier.

In some embodiments, the acidic amino acid as described herein is selected from the group consisting of glutamic acid (GA) and aspartic acid (AA).

In some embodiments, a cobalt-containing complex with an acidic acid amino acid as described herein is a cobalt-containing glutamic acid (COGA) complex or a cobalt-containing aspartic acid (COAA) complex.

In some embodiments, a cobalt-containing complex with an acidic acid amino acid as described herein is represented by Formula I Formula I

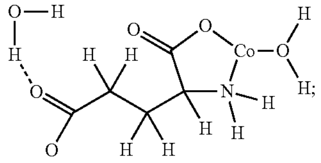

or.

C5 H11 Co N O6

Formula II

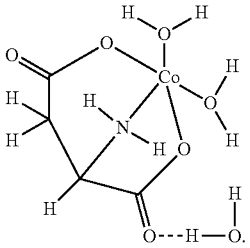

C4 H11 Co N O7

In some embodiments, the cobalt-containing complex is in the form of crystals.

In some embodiments, the cancer is selected from the group consisting of liver cancer (hepatoma), brain cancer (glioblastoma), skin cancer (melanoma), lung cancer, head and neck cancer, breast cancer, cervical cancer, colon cancer, gastric cancer, leukemia, kidney cancer, ovarian cancer, pancreatic cancer, prostate cancer, and testicular cancer.

In some embodiments, the cobalt-containing complex is administered in an amount effective in inhibiting proliferation of the cancer cells.

In some embodiments, the cobalt-containing complex is administered in an amount effective in inhibiting expression of myca, mycb, cdk1, cdk2, ccnd1 and/or ccne1 in the cancer cells.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments. It should be understood, however, that the invention is not limited to the preferred embodiments shown. In the drawings:

FIG. 3A shows the feeding protocol of zebrafish larva. FIG. 3B shows that tert overexpression induces the expression of ccne1. FIG. 3C shows that tert overexpression induces the expression of cdk1. FIG. 3D shows that tert overexpression induces the expression of cdk2. FIG. 3E shows that tert overexpression induces the expression of ccnd1. FIG. 3F shows that tert overexpression induces the expression of myca. FIG. 3G shows that tert overexpression induces the expression of mycb.

DETAILED DESCRIPTION OF THE INVENTION

Figure 1:
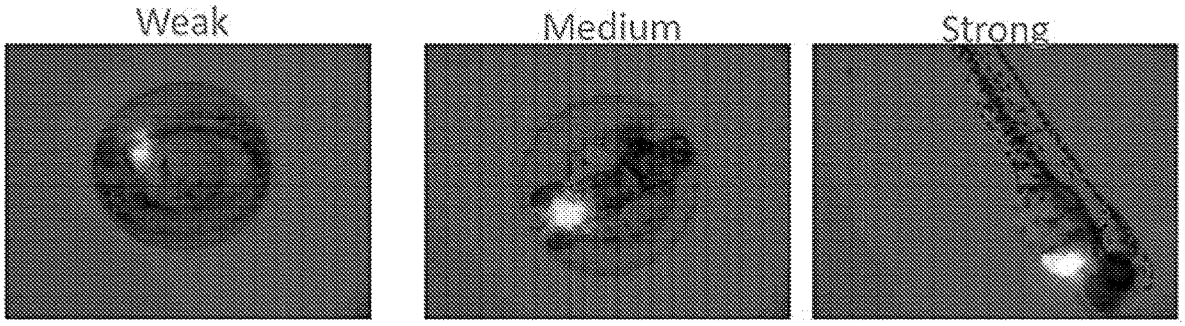
FIG. 1 shows that GFP expression in the tert transgenic fish with the fluorescence intensity (weak, medium or strong) as reporter for the transgene's expression.

The following description is merely intended to illustrate various embodiments of the invention. As such, specific embodiments or modifications discussed herein are not to be construed as limitations to the scope of the invention. It will be apparent to one skilled in the art that various changes or equivalents may be made without departing from the scope of the invention.

In order to provide a clear and ready understanding of the present invention, certain terms are first defined. Additional definitions are set forth throughout the detailed description. Unless defined otherwise, all technical and scientific terms used herein have the same meanings as is commonly understood by one of skill in the art to which this invention belongs.

As used herein, the singular forms "a", "an", and "the" include plural referents unless the context clearly dictates otherwise. Thus, for example, reference to "a component" includes a plurality of such components and equivalents thereof known to those skilled in the art.

The term "comprise" or "comprising" is generally used in the sense of include/including which means permitting the presence of one or more features, ingredients or components. The term "comprise" or "comprising" encompasses the term "consists" or "consisting of."

Cobalt is an essential trace element existing in all animals mainly in the form of vitamin B12, cobalamin, and plays an important role in several biological processes. Many investigations show the participations of cobalamin with different forms are necessary for DNA synthesis and regulation, development of red blood cells, and maintaining normal brain and nerve function. Cobalt is less toxic than nonessential metals such as platinum.

Acidic amino acids are a type of polar amino acids which contain having a negative-charged side chain. In particular, these amino acids have two carboxylic groups in the amino acid structure: one carboxylic group in the side chain and the other attached to the central carbon atom. Examples of acidic amino acids are glutamic acid and aspartic acid.

Glutamic acid (GA) is of the chemical formula $C_5H_9NO_4$ and molar mass of 147.130 g·mol−1. Glutamic acid and its derivative, glutamine, are found to be essential for rapid growth of cancer cells. Glutamic acid is converted into glutamine in an energy dependent reaction by glutamine synthetase inside the human body. In tumor genesis, glutamine is a nitrogen donor in the nucleotide and amino acid biosynthesis. It also helps the uptake of essential amino acid, maintains the activation of TOR kinase, supports the NADPH production and acts as the respiratory fuel in tumor cells.

Aspartic acid (AA) is of the chemical formula $C_4H_7NO_4$ and molar mass of 133.103 g·mol−1. Aspartate acts as a precursor in nucleotide synthesis and plays an important role in cell proliferation. Furthermore, there are many reports point out aspartate becomes a limiting factor in tumor growth and cancer cell survival by suppressing mitochondrial metabolism. Moreover, the sensitivity or resistance to various therapeutics in the clinic or in clinical trials are shown to related with aspartate availability.

The present invention is based, at least in part, on the finding that a cobalt-containing acidic amino acid complex is effective in inhibiting cancer cell growth.

As described herein, a cobalt-containing complex with an acidic amino acid is a complex of cobalt with an acidic amino acid such as glutamic acid or aspartic acid. Specifically, cobalt as used herein can be in common oxidation states such as +2 (cobalt(II) and +3 (cobalt(III). Glutamic acid and aspartic acid as used herein can be of the L or D configuration, as well as mixtures of rotamers as appropriate.

In certain embodiments, a cobalt-containing complex with an acidic acid amino acid as described herein is a cobalt-containing glutamic acid (COGA) complex or a cobalt-containing aspartic acid (COAA) complex.

In some embodiments, a cobalt-containing complex as described herein is of the formula I (COGA) as follows Formula I

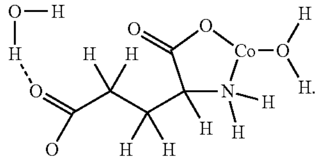

C5 H11 Co N O6

In some embodiments, a cobalt-containing complex as described herein is of the formula II (COAA) as follows Formula II

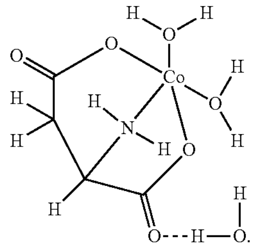

C4 H11 Co N O7

A cobalt-containing complex as described herein can be prepared by a method as previously described, for example, in Yugen Zhang et al. 2003, CrystEngComm. 5(5):34-37. Briefly, cobalt (II) chloride-6-hydrate in water is added to an aqueous solution containing glutamate or aspartate and the mixture is kept for a period of time sufficient to form a mixture of cobalt with glutamic acid or aspartic acid.

In some embodiments, a cobalt-containing complex as described herein is a hydrate or anhydrous.

In some embodiments, the cobalt-containing complex is in the form of crystals.

In some embodiments, the cobalt-containing complex is a cobalt-containing glutamic acid (COGA) complex in the form of crystals having a molecular packing arrangement defined by space group P2 and unit cell dimensions a=7.1 A°, b=10.4 A°, and c=11.2 A°.

In some embodiments, the cobalt-containing complex is a cobalt-containing aspartic acid (COAA) complex in the form of crystals having a molecular packing arrangement defined by a=7.7 A°, b=9.3 A°, and c=11.5 A°

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like).

The term "treating" as used herein refers to the application or administration of a composition including one or more active agents to a subject afflicted with a disorder, a symptom or conditions of the disorder, or a progression of the disorder, with the purpose to cure, heal, alleviate, relieve, alter, remedy, ameliorate, improve, or affect the disorder, the symptoms or conditions of the disorder, the disabilities induced by the disorder, or the progression of the disorder or the symptom or condition thereof.

The term "effective amount" used herein refers to the amount of an active ingredient to confer a desired therapeutic effect in a treated subject. For example, an effective amount for treating cancer can be an amount that can prohibit, improve, alleviate, reduce or prevent one or more symptoms or conditions or progression thereof. In some embodiments, an effective amount as used herein can be an amount effective in inhibiting growth and/or inducing apoptosis of cancer cells. In some embodiments, an effective amount as used herein can be an amount effective in inhibiting expression of myca, mycb, cdk1, cdk2, ccnd1 and ccne1 in the cancer cells. Preferably, the effective amount does not incur side effects in the patients such as cytotoxicity to normal cells.

The therapeutically effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience.

For purpose of deliver, a therapeutically effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

According to the present invention, a cobalt-containing complex as described herein may be used as an active ingredient for treating cancer. Examples of cancer to be treated include but are not limited to liver cancer (hepatoma), brain cancer (glioblastoma), skin cancer (melanoma), lung cancer, head and neck cancer, breast cancer, cervical cancer, colon cancer, gastric cancer, leukemia, kidney cancer, ovarian cancer, pancreatic cancer, prostate cancer, and testicular cancer.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

Example 1

Previous studies have found that after human tumor cell xenotransplant into zebrafish embryos by injection to 2 days post-fertilization embryos, the proliferation and migration behavior of tumor cells in zebrafish embryos is similar to that in human patients. Therefore, we used xenotransplantation model, treat the embryos with a cobalt-containing glutamic acid (COGA) complex to test the anti-proliferation and anti-migration effect of COGA. Up to 60% of liver cancer patients have found a mutation in the telomerase reverse transcriptase (TERT) promoter in liver cancer. This mutation can lead to overexpression of telomerase in liver cancer cells, and promote the growth of cancer cells. We had established a liver-specific tert over-expression transgenic fish, and used qPCR to analyze the cell proliferation genes (ccne1/cdk1/cdk2) in the tert transgenic fish 15 days after fertilization. Compared with wild species of zebrafish, there was a significant increase. In addition, β-catenin downstream genes (ccnd1/myca/mycb), which are closely related to the formation of liver cancer, also increased significantly. Therefore, we used tert transgenic fish HCC model fed with COGA to test the effect of COGA in inhibiting liver cancer. We also used liver red fluorescent transgenic zebrafish embryos to test the hepatotoxicity of COGA, and used zebrafish embryos to examine the embryo toxicity of COGA. We compared normal liver cells and liver cancer cells, to test whether COGA is an effective and safe personalized treatment for liver cancer. Further, we tested whether COGA is effective in inhibiting growth of various cancer cells.

1. MATERIAL AND METHODS 1.1 Preparation and Structural Determination of a Cobalt-Containing Glutamic Acid (COGA) Complex and a Cobalt-Containing Aspartic Acid (COAA) Complex The preparation was performed based on Yugen Zhang et al. 2003, CrystEngComm. 5(5):34-37. Briefly, to an aqueous solution (25 ml) containing L-glutamate (0.735 g) was added $Co(ClO_4)_2 \cdot 6H_2O$ (1.830 g) in water (5 ml) at 25° C. The pH of the resulting solution was adjusted to 7.5 using dilute NaOH and kept at 60° C. for several hours to prepare the L-glutamate complex.

1 mL COGA solution was placed in 1 mL Eppendorf at 25° C., and 0.05 g red purple crystals were obtained by slow evaporation after 30 days. The crystal was analyzed by X ray diffraction as follows.

A red purple ellipse-like specimen of $C_5H_{11}CoNO_6$, approximate dimensions 0.101 mm×0.165 mm×0.370 mm, was used for the X-ray crystallographic analysis. The single-crystal X-ray diffraction data of the crystal was collected in-house on a Bruker D8 Venture diffractometer equipped with a Mo-target (Kα=0.71073 Å) microfocus X-ray generators and a PHOTON-II CMOS detector. The temperature was adjusted at 200 K with a nitrogen flow (Oxford Cryosystems). After collection, the data were integrated with the Bruker SAINT software package using a narrow-frame algorithm and were corrected for absorption effects using the Multi-Scan method (SADABS). Then, the molecular structure was solved and refined by the Bruker SHELXTL Software Package and the final anisotropic full-matrix least-squares method was used to refine on $F^2$ with variables parameters to determine crystal structure, using the space group P 21 21 21 (orthorhombic), with Z=4 for the formula unit, $C_5H_{11}CoNO_6$. The final cell constants of a=7.12700 (10) Å, b=10.4397(3) Å, c=11.2621(3) Å, volume=837.94 (3) $Å^3$, are based upon the refinement of the XYZ-centroids of 7520 reflections above 20 σ(I) with 5.715°<2θ<66.97°. The final anisotropic full-matrix least-squares refinement on $F^2$ with 163 variables converged at R1=2.76%, for the observed data and wR2=7.59% for all data. The ratio of minimum to maximum apparent transmission was 0.798. The calculated minimum and maximum transmission coefficients (based on crystal size) are 0.5180 and 0.8200.

The stock solution of COGA is 100 mM solution in $ddH_2O$ stored at room temperature. In this study, we used 0.5× working concentration equilibrate to 0.05 mM (50 μM) or 1× working concentration equilibrate to 0.1 mM (100 μM).

A cobalt-containing aspartic acid (COAA) complex was prepared in a similar process.

1.2 Wild Type and Transgenic Zebrafish Lines

Wild type AB strain (WT) zebrafish and three transgenic zebrafish lines, Tg(fabp10a:tert:cmlc2:GFP), Tg(fli1:EGFP), Tg(fabp10a:EGFP-mCherry, were used in this study.

The Tg(fli1:EGFP) transgenic fish expressed EGFP protein under the control of endothelial promote (fli1) was generated as previously described (*Developmental biology* 248, 307-318, doi:10.1006/dbio.2002.0711 (2002)). The Tg(fabp10a:EGFP-mCherry) express EGFP-mCherry fusion protein under the control of liver specific promoter (fabp10a) was generated as previously described (*PLoS One* 8, e76951, doi:10.1371/joumal.pone.0076951 (2013)).

The Tg(fabp10a:tert:cmlc2:GFP) transgenic fish expressed GFP protein under the control of combinational promoter including fatty acid binding protein 10a (fabp10a), telomerase reverse transcriptase (tert) and cardiac myosin light chain 2 (cmlc2) was generated as previously described (*Developmental dynamics: an official publication of the American Association of Anatomists* 236, 3088-3099, doi: 10.1002/dvdy.21343 (2007)). Specifically, the tert gene was amplified from zebrafish tert cDNA cloned from Rapid amplification of cDNA ends (RACE), and middle entry clone: pME-tert was produced which was used to generate the expression construct by LR reaction together with p5E-fapb10a, p3E-pA, and pDEST-Tol2-CG2. The expressing plasmid—pTol2-fabp10a-tert-pA/CG2 was purified and after confirming the sequencing was microinjected to AB wild type zebrafish. The embryos carrying the transgene were selected by screening the green fluorescent protein expression in the heart at three days post-fertilization (dpf). The transgenic fish were raised to sexual mature (around 3 months) and crossed with AB wild-type fish to generate F1 fish, and then self-crossed to get F2 transgenic fish. We used fin-clip method to ensure all the transgenic fish has tert DNA insertion and overexpress tert mRNA by qPCR. All experiments in this study were performed using F2 homozygous fish.

Zebrafish (*Danio rerio*) were maintained in the Zebrafish Core Facility at NTHU-NHRI (ZeTH). The zebrafish were incubated at 28° C. under continuous flow in the zebrafish core facility and with automatic control of a 14 hour light/10 hour dark cycle. All zebrafish experiments were performed under the approval of the Institutional Animal Care and Use Committee (IACUC) at NHRI.

1.3 Embryo Collection and Embryonic Toxicity Test

One day prior to fertilization, male and female adult AB(WT) and tert transgenic zebrafish were placed individually into mating tanks with the inner mesh. Male and female fish were separated by a separator and left in mating cages overnight. The next morning after removal of the separator, the zebrafish were stimulated by the light, and the male started to chase female and the sperm fertilized the egg. After 1 hour, the embryos were collected and transferred to a 100-mm dish with E3 solution (5 mM NaCl, 0.17 mM KCl, 0.33 mM CaCl2, 0.33 mM MgSO4, pH 7.0) incubated at 28° C. At 16-22 hpf, embryos were washed with 0.0016% bleach solution to clean and improve the survival rate of embryos. The unfertilized and dead embryos were removed at 6 hours post-fertilization, and the remaining live embryos were replenished with fresh E3 solution and kept for incubation.

1.4 Feeding Protocol and COGA Treatment 50 zebrafish larva were placed in a fish tank with 800 ml of system water, the water were refreshed every day at 4 pm. From day 5 to day 15, AB(WT) and tert transgenic zebrafish were fed with normal larva food, plus 20 ml of Paramecium, and there must be 2 hours between meals, four meals a day. The last meal must be fed after 1 hour before the water changed. The zebrafish larva were placed in a petri dish containing 25 ml of clean E3 water (control group) or 0.5×COGA in E3 water, soak the larva in the drug overnight until 9 o'clock the next morning, and then move the fish to 800 ml fish tank for system water. The fish were fasting for one days before collecting the samples for RNA extraction and hematoxylin-eosin (H&E) staining.

1.5 Liver Tissue Collection and Paraffin Section

After 1 month of RO injection, the fish was sacrificed, and the liver was taken out and divided into two parts for RNA isolation and paraffin section. The liver tissues were frozen in liquid nitrogen immediately after sectioning and stored at −80° C. for later RNA isolation. For histochemistry analysis, liver tissues were fixed in a 10% formalin solution (Sigma-Aldrich Inc., St. Louis, MO, USA). The fixed tissue was embedded in paraffin, and sectioned at 5-μm thickness mounted on poly-L-lysine coated slides, and the sections were stained with hematoxylin and eosin (H&E stain), which this part was performed by the Pathology core facility.

1.6 Total RNA Isolation

Total RNA was isolated by NucleoSpin® RNA kit (MACHEREY-NAGEL, USA). About 30 mg of tissue was collected and placed in 350 μl buffer RA1 and 3.5 μl β-mercaptoethanol (Sigma-Aldrich, USA) mixture, which the samples can be stored at −80° C. at this step. Upon RNA isolation, the samples were thawed slowly in room temperature and then disrupted by pestles to lyse tissue. The lysate was filtrated with NucleoSpin® Filter (violet ring) by centrifuging at 11000 g for 1 minute to reduce viscosity and clear the lysate. After centrifugation, the filtrate was added with 350 μl of 70% ethanol prepared by DEPC water (diethyl pyrocabonate water) and mixed well by pipetting up and down. The lysate was loaded to NucleoSpin® RNA column (light blue ring) and centrifuged at 11000 g for 30 seconds. Following, the membrane desalting buffer with 350 μl was added to the column and centrifuged at 11000 g for 1 minute.

Each column was added with 95 μl DNase reaction mixture contained 10% RNase-free DNase and 90% reaction buffer for DNase, and placed at room temperature for 30 minutes to digest the genomic DNA. After DNase digestion, 200 μl buffer RAW2 was added to the column for inactivating the DNase and centrifuged at 11000 g for 30 seconds. Then the columns contained RNA were transferred to new 2 ml collection tubes, and 600 μl and 250 μl buffer RA3 were added sequentially followed by centrifuged at 11000 g for 30 seconds and 2 minutes to clean-up the RNA samples twice. Finally, the columns were transferred into new 1.5 ml tubes which are RNase free and eluted the RNA samples in 40 μl RNase-free $H_2O$ and then centrifuged at 11000 g for 1 minute. All RNA samples were stored at −80° C.

1.7 Reverse Transcription-Polymerase Chain Reaction (RT-PCR)

Complementary DNA (cDNA) was synthesized by High Capacity RNA-to-cDNA Kit (Applied Biosystems, USA).

Reverse Transcription (RT) Reaction mixture is as follows:

| | |
|---|---|
| 2X RT Buffer | 10 μl |
| 20X Enzyme Mix | 1 μl |
| RNA sample | 1 μg |
| RNase-free $H_2O$ | Quantity replenish to 20 μl |
| Total volume | 20 μl |

The reverse transcription in thermal cycling program in the PCR machine was set as following: 37° C. for 60 minutes to start RT reaction→95° C. for 5 minutes to inactive enzyme activity→4° C. for preservation. For long-term storage, we put the samples in a −20° C. freezer.

1.8 Quantitative Polymerase Chain Reaction (Q-PCR)

After the RT was finished, diluted the cDNA to 100× with RNase free water. For each sample, the following reaction mixture was added to one well of 384-well Q-PCR plate:

| | |
|---|---|
| Quantitative Real-Time PCR Reaction mixture: cDNA (diluted with RNase free water) | 3.8 μl |
| Primer mix (Forward and Reverse) 2.5 μM | 1.2 μl |
| 2x SybrGreen Mix | 5.0 μl |
| Total | 10.0 μl |

The 2× SybrGreen was added last, because it is photosensitive. The Q-PCR program was set as following in ABI HT-7900 machine:

1. Stage I: 50° C.—2 minutes, 95° C.—5 minutes, 4° C.—forever.
2. Stage II: 95° C.—10 minutes
3. Stage III (40 cycles): 95° C.—15 sec
   60° C.—1 minute
4. Stage IV: 95° C.—15 sec
   60° C.—15 sec
   95° C.—15 sec The resulting first-strand cDNA was used as a template for qualitative PCR in triplicate by using the SYBR Green Q-PCR Master Mix Kit (Applied Biosystems) using an ABI PRISM 7900 System. After normalization to internal control actin, the expression ratio between the experimental and control groups was calculated using the comparative Ct method. The relative expression ratio (fold change) was calculated based on ΔΔCt, $\Delta\Delta Ct=(Ct_{target}-Ct_{actin})_{treatment}-(Ct_{target}-Ct_{actin})_{control}$, and fold change$=2^{-\Delta\Delta Ct}$. All experiments were performed in triplicate, and the mean values of three values are presented. At least three independent samples were used for Q-PCR, and the standard error was calculated and incorporated into the presented data as medians±standard error. Differences among variables were assessed by a two-tailed Student's t test. A $P<0.05$ was considered statistically significant and is shown as: *: $0.01<P\leq0.05$; : $0.001<P\leq0.01$; and *: $P\leq0.001$.

1.9 Xenotransplantation Assay to Examine Cell Proliferation and Migration in Zebrafish The fertilized eggs of AB(WT) zebrafish were incubated at 28° C. in E3/PTU solution and raised under the standard zebrafish laboratory condition. Zebrafish embryos of 2 days post-fertilization were dechlorinated and anesthetized with 0.016% tricaine (MS-222) before microinjection. The 293T/EDN1 cells collected in PBS were labeled in vitro with CM-Dil (red fluorescence) (Vybrant; Invitrogen, Carlsbad, CA, USA). Each injection volume was 4.6 nl contained about 200 cells and implanted into each yolk of 2 dpf zebrafish embryo via glass capillary using a Nanoject II™ nanoliter injector (Drummond Scientific). After injection, zebrafish embryos were washed once with E3/PTU solution, and incubated for 1 hour at 28° C. and checked for presence of fluorescent cells at 2 hours post transplantation. After 24 hours post transplantation, the zebrafish were treated with 0.5×COGA, and observed the cell proliferation and migration abilities in following 3-5 days using a fluorescent microscope (LEICA DM IRB).

1.10 Hepatoxicity Assay

EGFP-mCherry embryos collection and incubation conditions were mentioned as above. About 3 dpf, 50 embryos were distributed into 10 ml chemical solution/well (chemical/E3 solution) in 6-well plates until 5 dpf and new chemical solution was replaced every day. At 5 dpf, embryos were anesthetized with tricaine (0.016%) and the images of 8 to 10 embryos randomly per well were taken by ZEISS AxioCam MRc. There are three different images which one with auto exposure-time for the clearest view, one with fixed exposure-time to capture RFP (red fluorescent protein) intensity below saturation for intensity measurement and comparison, and the last one with sufficient exposure-time to show the whole liver region for size measurement. Image J software was then used to quantify intensity of RFP and liver size. Average RFP intensity in the liver was calculated and compared within the same group of lateral view fry under the same magnification and fixed exposure-time.

1.11 Statistical Analysis

The statistical analysis of the results was performed using a two-tailed Student's t test. In all statistical analyses, A p-value<0.05 was considered to be statistically significant and is shown as: *: $0.01<P\leq0.05$; : $0.001<P\leq0.01$; and *: $P\leq0.001$.

1.12 Cell Proliferation Assay I

U-87 MG cells (a human primary glioblastoma cell line) were cultured in MEM medium (Gibco, New York, NY, USA). A375 cells (a human melanoma cell line) and Huh7 cells (a human hepatocellular carcinoma (HCC) cell line) were cultured in DMEM medium (HyClone, Logan, UT, USA). The culture media were supplemented with 10% heat-inactivated fetal bovine serum (FBS), 1% penicillin/streptomycin and 1% glutamate (HyClone, Logan, UT, USA). Cells were seeded in 96-well plates at a density of 2000 cells/well. Then, cells were transferred to 37° C. incubator. After 24 h, cells were treated with indicated concentrations of COGA for 72 h. At the end of incubation, the PrestoBlue™ Cell Viability Reagent (Invitrogen, Eugene, OR, USA) was distributed to cells. The plates were incubated for 90 min at 37° C. in a humidified, 5% CO2 atmosphere and the fluorescence was then recorded at Ex/Em: 560 nm/590 nm. Triplicate experiments were performed.

1.13 Cell Proliferation Assay II

Human lung cancer cell line NCI-H226 was purchased from the American type culture collection (CRL-5826). NCI-H226 was grown in RPMI supplemented with 10% FBS in a humidified atmosphere containing 5% CO2 at 37° C. Human melanoma cell line A375, human pharynx squamous cell carcinoma FaDu, human cervical epithelioid carcinoma HeLa and human chronic myelogenous leukemia K-562 were purchased from Bioresource Collection and Research Center (BCRC), Hsinchu 300, Taiwan. A375 cells were grown in DMEM supplemented with 10% FBS in a humidified atmosphere 5% $CO_2$ at 37° C. FaDu cells were grown in DMEM supplemented with 10% FBS in a humidified atmosphere 5% $CO_2$ at 37° C. HeLa cell were grown in DMEM supplemented with 10% FBS in a humidified atmosphere 5% $CO_2$ at 37° C. K-562 cells were grown in IMDM supplemented with 10% FBS in a humidified atmosphere containing 5% $CO_2$ at 37° C. U87 cells were grown in EMEM supplemented with 10% FBS in a humidified atmosphere containing 5% $CO_2$ at 37° C.

The COGA compound was prepared as 100 mM stock solution in $ddH_2O$ and stored at room temperature (RT) when not in used. The COGA 100 mM stock solution was diluted into appropriated working concentration 24 h after cell seeding. The highest working concentration of compound was set at 100 mM stock solution $ddH_2O$. From this highest working concentration, a serial three-fold dilution for seven points was performed with $ddH_2O$, and then diluted 5× further with culture medium. All eight concentrations were at 2× the final concentration required. 100 μl of diluent was added to the well containing 100 μl of medium. The same series of dilutions was prepared without addition of cells as background control samples. The final concentration was ranging from 10 mM to 0.00457 mM. Final $ddH_2O$ concentration was 10%.

Exponential grown cells were harvested and re-suspended in the culture medium. The suspended cells were seeded in 96-well tissue culture plates at optimized cell number per well and incubated at 37° C., 5% CO2 humidified atmosphere overnight. On the following day, aliquots (typically 100 μL) of the culture medium containing diluted compound solution were added to wells of the 96-well tissue culture plates. Cells for positive control (vehicle control) were treated with 10% ddH2O in culture medium. Each diluted compound solution was tested in triplicate. The plates were incubated at 37° C., 5% CO2, under humidified atmosphere for 72 hours. After incubation, cells viability was examined by Cell Titer 96 Aqueous Non-Radioactive Cell Proliferation Assay (Promega). The living cells were detectable by conversion of MTS into aqueous, soluble formazan.

MTS/PMS solution was freshly prepared and added (20 μl per well) into each well of 96-well cultured plate. The assay plate was incubated for 3 hours at 37° C., 5% CO2, under humidified atmosphere, and measured the absorbance at 490 nm using Multiskan™ GO Microplate Spectrophotometer (Thermo Fisher Scientific).

Corrected absorbance values were obtained by subtracting the average 490 nm absorbance of the negative control wells (medium only, no cell, as background control) from all other absorbance values. Percentage inhibition of cell growth for compound treatment was calculated using this formula:

% inhibition=100%×{1−[(absorbance of the treated wells−absorbance of the negative control wells)/(absorbance of the positive control wells−absorbance of the negative control wells)]}.

The sigmoidal dose-response curve is generated by fitting the percentage inhibition value as a function of logarithm of compound concentrations using GraphPad Prism software (v.5.0). IC50 values are defined as the concentration needed for a 50% inhibition of cell growth. The test is performed in triplicate for two times.

2. RESULTS

2.1 COGA and COAA

COGA and COAA solutions were prepared and crystals were obtained and analyzed by X ray diffraction. The data of the X ray diffraction is as follows.

COGA

| Crystal data | | |
|---|---|---|
| Empirical formula | C5 H11 Co N O6 | |
| Formula weight | 240.08 | |
| Crystal system | Orthorhombic | |
| Space group | $P2_12_12_1$ | |
| Unit cell dimensions | a = 7.12700(10) Å | α = 90°. |
| | b = 10.4397(3) Å | β = 90°. |
| | c = 11.2621(3) Å | γ = 90°. |
| Volume | 837.94(3) $Å^3$ | |
| Z | 4 | |
| F(000) | 492 | |
| Density (calculated) | 1.903 $Mg/m^3$ | |
| Wavelength | 0.71073 Å | |
| Cell parameters reflections used | 6952 | |
| Theta range for Cell parameters | 2.86 to 28.31°. | |
| Absorption coefficient | 2.047 $mm^{-1}$ | |
| Temperature | 200(2) K | |
| Crystal size | 0.370 × 0.165 × 0.101 $mm^3$ | |
| **Data collection** | | |
| Diffractometer | Bruker D8 Venture | |
| Absorption correction | Semi-empirical from equivalents | |
| Max. and min. transmission | 0.7457 and 0.5926 | |
| No. of measured reflections | 8384 | |
| No. of independent reflections | 2068 [R(int) = 0.0461] | |
| No. of observed [I > 2_igma(I)] | 2040 | |
| Completeness to theta = 25.242° | 99.0% | |
| Theta range for data collection | 3.383 to 28.307°. | |
| **Refinement** | | |
| Final R indices [ I > 2sigma(I)] | R1 = 0.0276, wR2 = 0.0758 | |
| R indices (all data) | R1 = 0.0279, wR2 = 0.0759 | |
| Goodness-of-fit on $F^2$ | 1.241 | |
| No. of reflections | 2068 | |
| No. of parameters | 163 | |
| No. of restraints | 4 | |
| Absolute structure parameter | 0.10(3) | |
| Largest diff. peak and hole | 0.359 and −0.347 e.$Å^{-3}$ | |
| **COAA** | | |
| Empirical formula | C4 H11 Co N O7 | |
| Formula weight | 244.07 | |
| Temperature | 200(2) K | |
| Wavelength | 0.71073 Å | |
| Crystal system | Orthorhombic | |
| Space group | $P2_12_12_1$ | |
| Unit cell dimensions | a = 7.7846(2) Å | α = 90°. |
| | b = 9.3456(3) Å | β = 90°. |
| | c = 11.5292(3) Å | γ = 90°. |
| Volume | 838.77(4) $Å^3$ | |
| Z | 4 | |
| Density (calculated) | 1.933 $Mg/m^3$ | |
| Absorption coefficient | 2.055 $mm^{-1}$ | |
| F(000) | 500 | |
| Crystal size | 0.200 × 0.056 × 0.046 $mm^3$ | |
| Theta range for data collection | 2.806 to 29.998°. | |
| Index ranges | −10 <= h <= 10, −13 <= k <= 13, −15 <= 1<= 16 | |
| Reflections collected | 13057 | |
| Independent reflections | 2437 [R(int) = 0.0526] | |
| Completeness to theta = 25.242° | 100.0% | |
| Absorption correction | Semi-empirical from equivalents | |
| Max. and min. transmission | 0.8749 and 0.6937 | |
| Refinement method | Full-matrix least-squares on $F^2$ | |
| Data/restraints/parameters | 2437/0/136 | |
| Goodness-of-fit on $F^2$ | 1.036 | |
| Final R indices [I > 2sigma(I)] | R1 = 0.0232, wR2 = 0.0549 | |

-continued

| | |
|---|---|
| R indices (all data) | R1 = 0.0256, wR2 = 0.0558 |
| Absolute structure parameter | −0.006(11) |
| Extinction coefficient | n/a |
| Largest diff. peak and hole | 0.259 and −0.304 e.Å$^{-3}$ |

2.2 Select the Tert Embryos with Similar Intensity for COGA Treatment and Identify the Dosage Based on Embryonic Toxicity At 48 hpf, fluorescent microscope was used to observe tert transgenic zebrafish embryos (FIG. 1), and the embryos with similar intensity of green fluorescent expressed in the heart were collected for further treatment. We choose the embryos with medium and strong fluorescence intensity for further experiment to make sure they have strong transgene (tert) expression.

Figure 2:
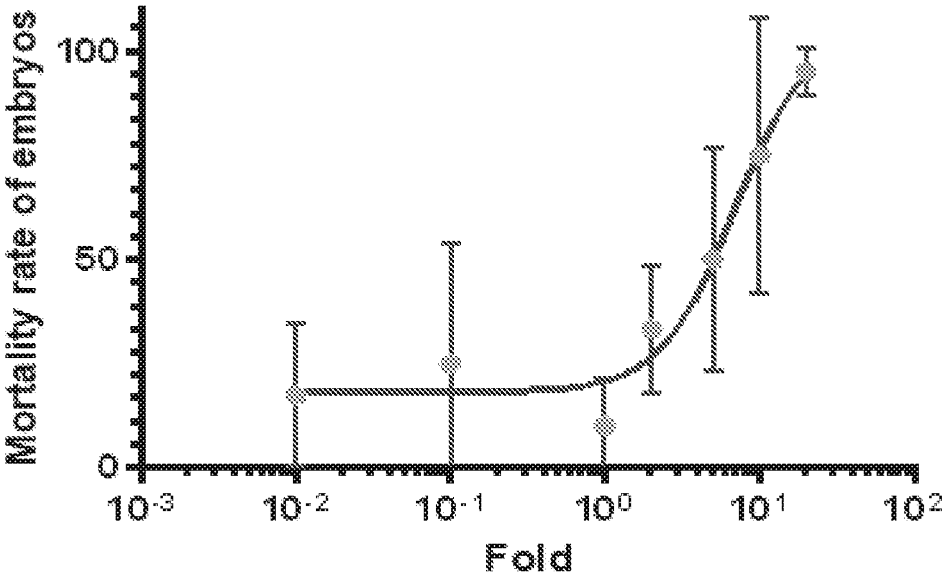
FIG. 2 shows the results of embryo toxicity assay of the tert transgenic fish treated with a cobalt-containing glutamic acid (COGA) complex.

Through embryo toxicity test experiments, we found that zebrafish embryos were immersed in a concentration of 0.01×(1 μM)–20×(2000 μM). The result is shown in FIG. 2. The mortality rate of embryos is 0.01×(1 μM), 0.1×(10 μM), and 1×(100 μM) are the lowest, so we choose 0.5×(50 μM) concentration of COGA for further experiment.

Figure 3A:
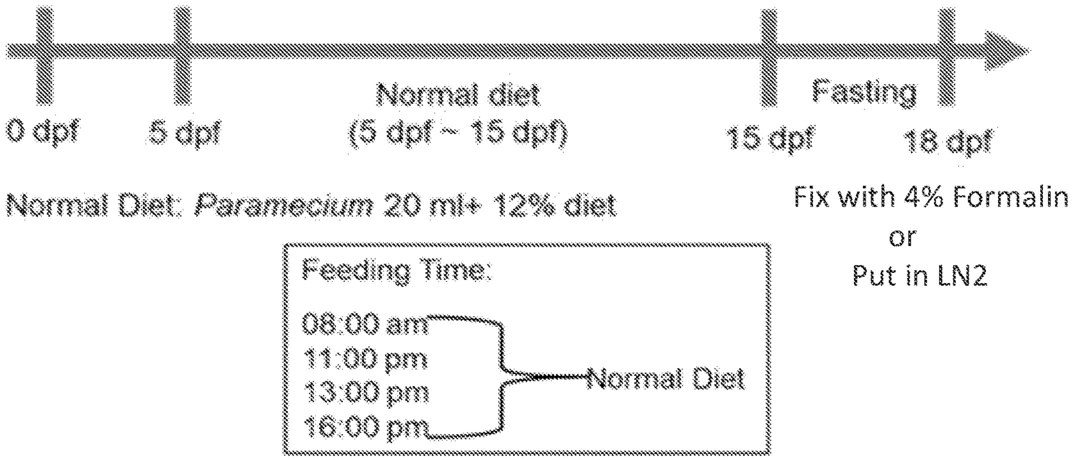
FIGS. 3A to 3G show that tert overexpression induces cell proliferation and β-catenin downstream target genes as early as 15 post-fertilization (dpf).
Figure 3B:
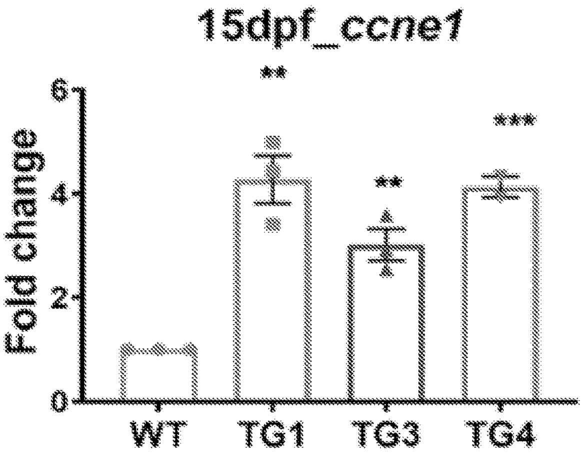
Figure 3C:
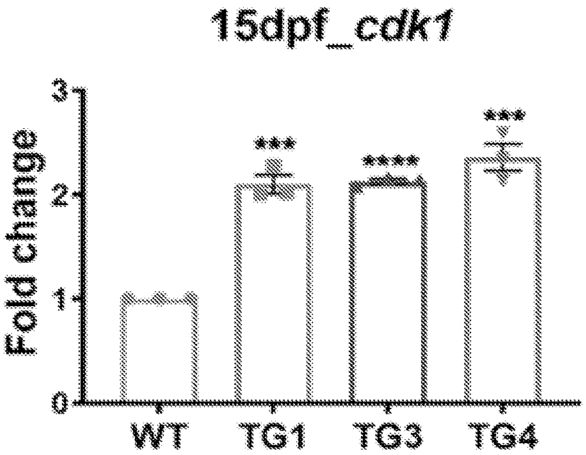
Figure 3D:
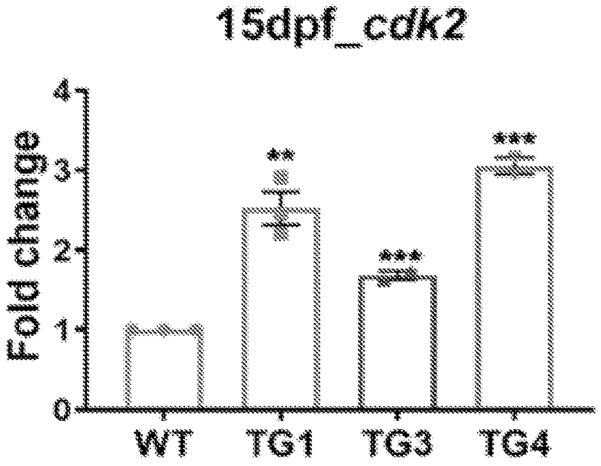

2.3 the Tert Overexpression Zebrafish can Induce Cell Proliferation and Activate β-Catenin Downstream Targets at 15 Dpf To investigate the effect of tert overexpression in the liver, we first examined tert transgenic fish at 15 days post fertilization under normal diet compared to WT larvae (FIG. 3A). Abnormal proliferation is one of the hallmarks in cancer[48]. The initiation of HCC depends on E-type cyclins E1 (CcnE1) and cyclin-dependent kinase 2 (Cdk2)[49]. Ccne1 overexpression caused liver tumor development in mice[50], Cdk2 plays a key role in cell cycle progression in hepatocyte[51], and cyclin-dependent kinase 1 (Cdk1) is essential for cell division of liver cancer[52]. Therefore, we examined the expression levels for ccne1, cdk1, and cdk2 as markers for cell cycle/proliferation by qPCR. The expression of cell cycle/proliferation markers (ccne1/cdk1/cdk2) was significantly increased compared to WT fish at 15 dpf (FIGS. 3B-D). This result indicated overexpression of tert in hepatocyte can promote cell proliferation.

Figure 3E:
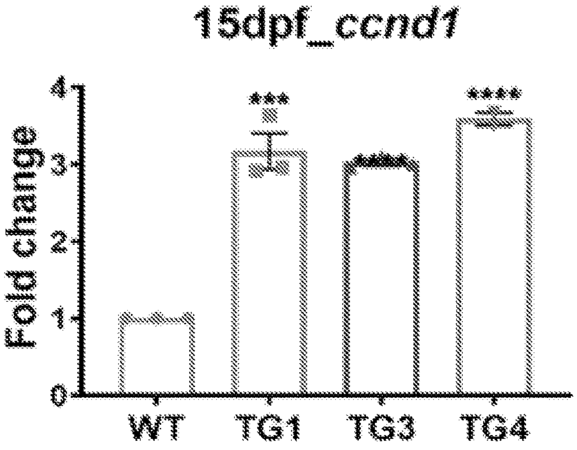
Figure 3F:
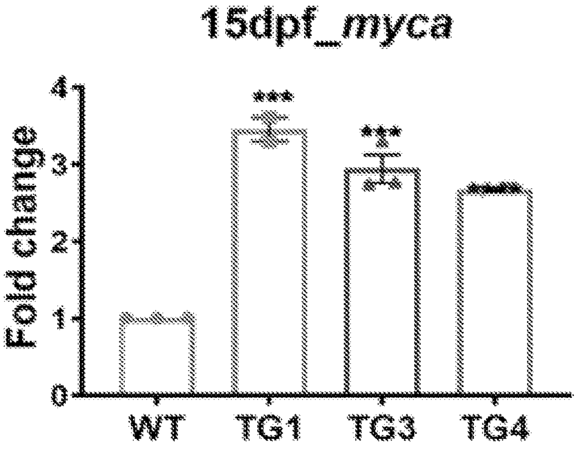
Figure 3G:
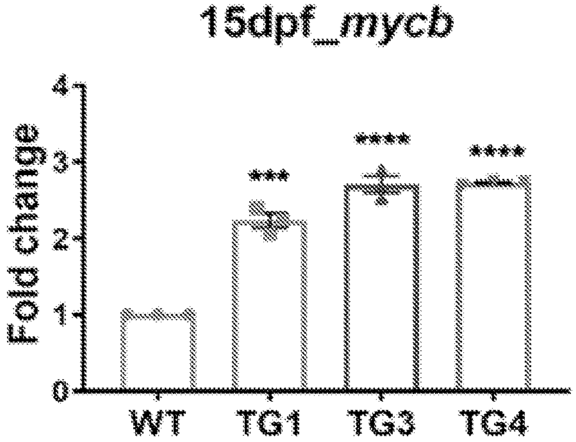

Previous research confirm the β-catenin is one of the primary oncogenes involved in HCC development[53], and the reactivated TERT acts as transcriptional modulator of Wnt/β-catenin signaling, resulting in the enhanced expression of β-catenin downstream target genes[54]. Therefore, we examined the expression levels of β-catenin downstream target genes (ccnd1/myca/mycb) in the 15 dpf tert transgenic fish. From our results, those β-catenin downstream target genes were also significantly upregulated in tert transgenic fish compared to wild-type fish (FIGS. 3E-G). These results indicated that tert overexpression induced the upregulation of cellular proliferation and activated β-catenin signaling pathway.

Figure 4:
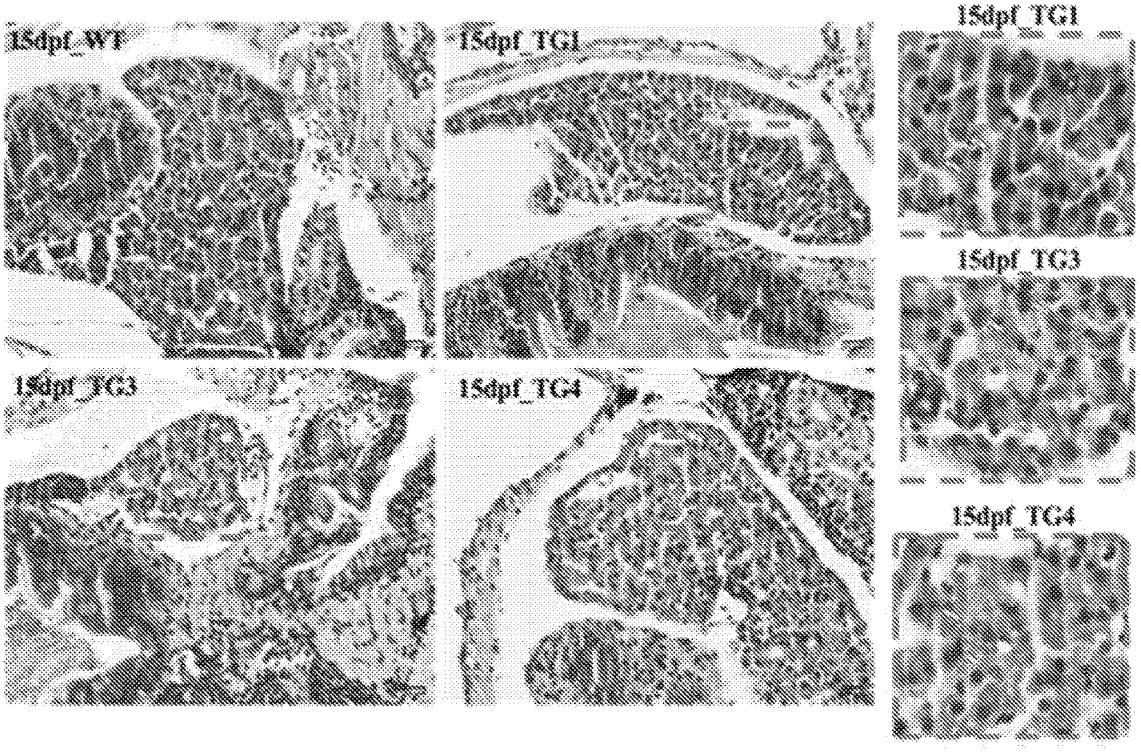
FIG. 4 shows the mitotic figure and trinucleated hepatocyte of tert transgenic fish and WT fish at 15 dpf.
Figure 4:
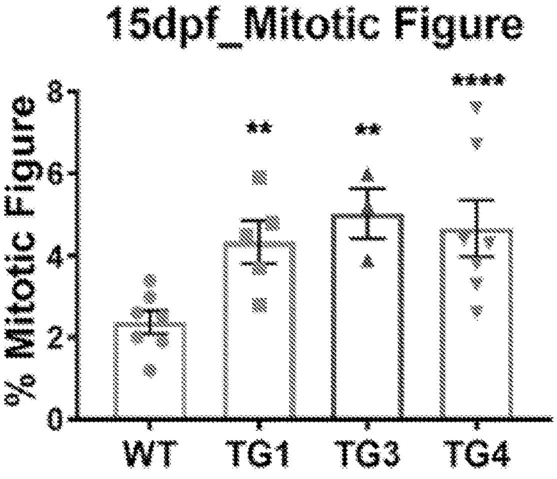
Figure 4:
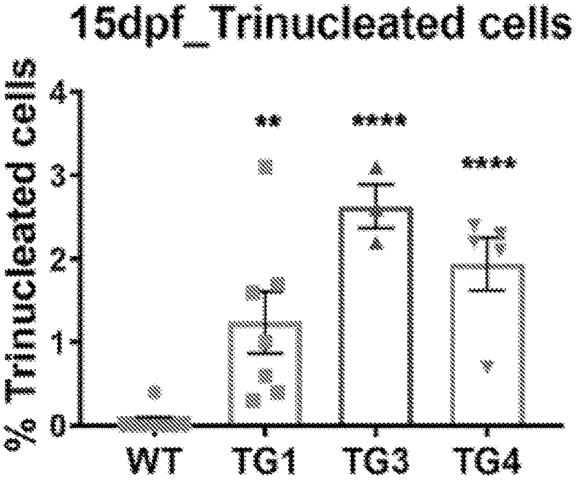

2.4 the Tert Overexpression Significantly Increased the Mitotic Figures and Trinucleated Cells in Zebrafish at 15 dpf To further confirm our finding, we used histopathology examination by H&E stain. In the H&E stain analysis (FIG. 4), we revealed that the ratio of mitotic figures and trinucleated cells in transgenic fish liver tissue had significantly increased compared with WT[55] (FIG. 4). Together with the qPCR results, these results indicated that the tert transgenic fish induced carcinogenesis in the early development stage in zebrafish larvae.

2.5 COGA Exhibits Anti-HCC Effect Against HCC Induced by Tert Overexpression

Figure 5:
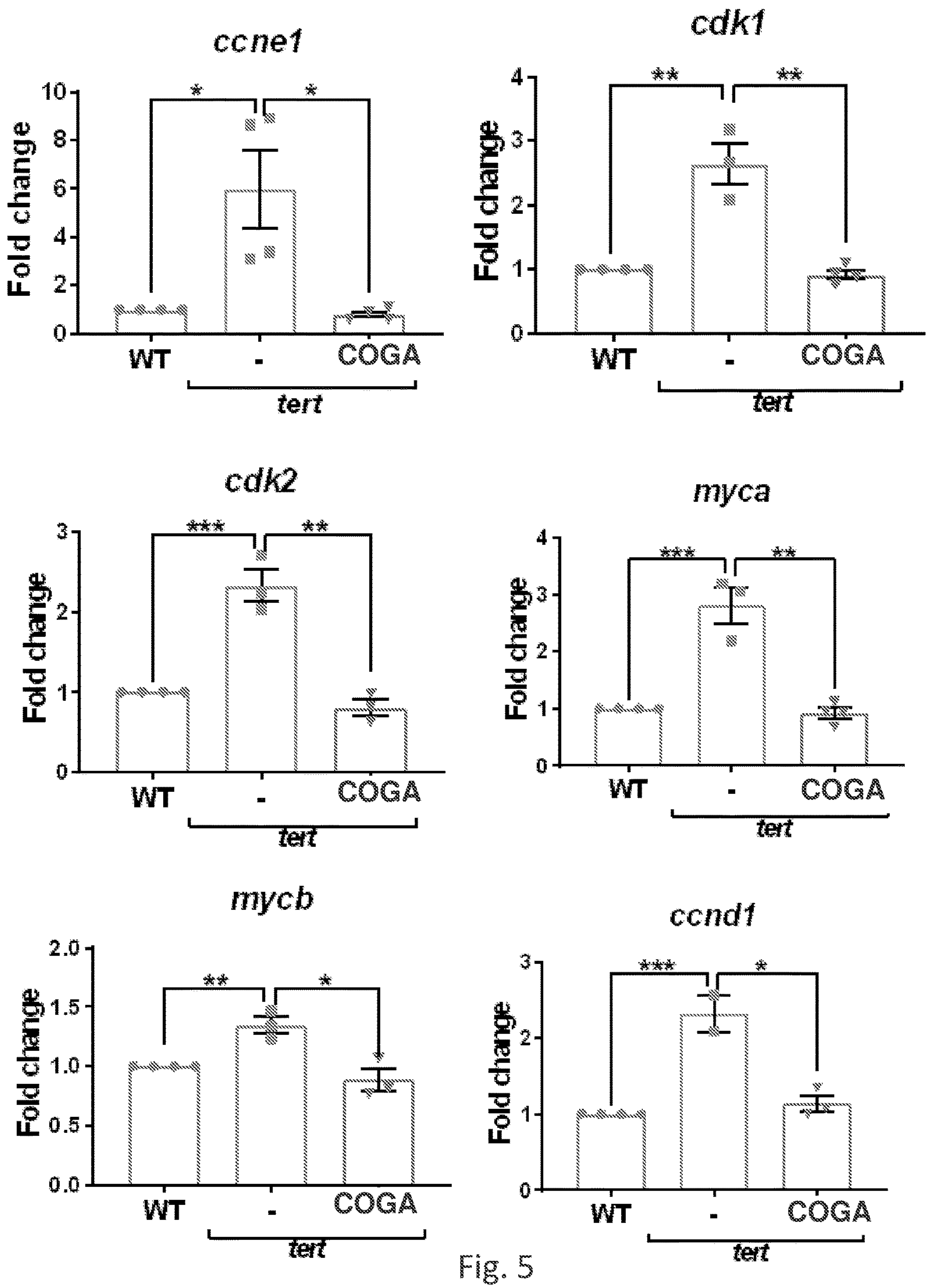
FIG. 5 shows that COGA treatment reduces the expression of cell proliferation and β-catenin downstream target genes (ccne1, cdk1, cdk2, myca, mycb and ccnd1) in tert transgenic fish at 15 dpf.

We fed wild-type and tert transgenic zebrafish with normal diet for 15 days, without or with 0.5×(50 μM) COGA, and analyze the expression of cell proliferation markers (ccne1, cdk1, cdk2), and beta-catenin downstream target genes (myca, mycb, ccnd1). As shown in FIG. 5, the gene expression of tert transgenic zebrafish without drug treatment is generally higher. In contrast, the gene expression of TERT zebrafish treated with COGA significantly reduced the expression of cell proliferation markers and beta-catenin downstream target genes. Therefore, it is suggested that COGA is an effective drug to inhibit liver cancer in tert transgenic zebrafish.

Figure 6:
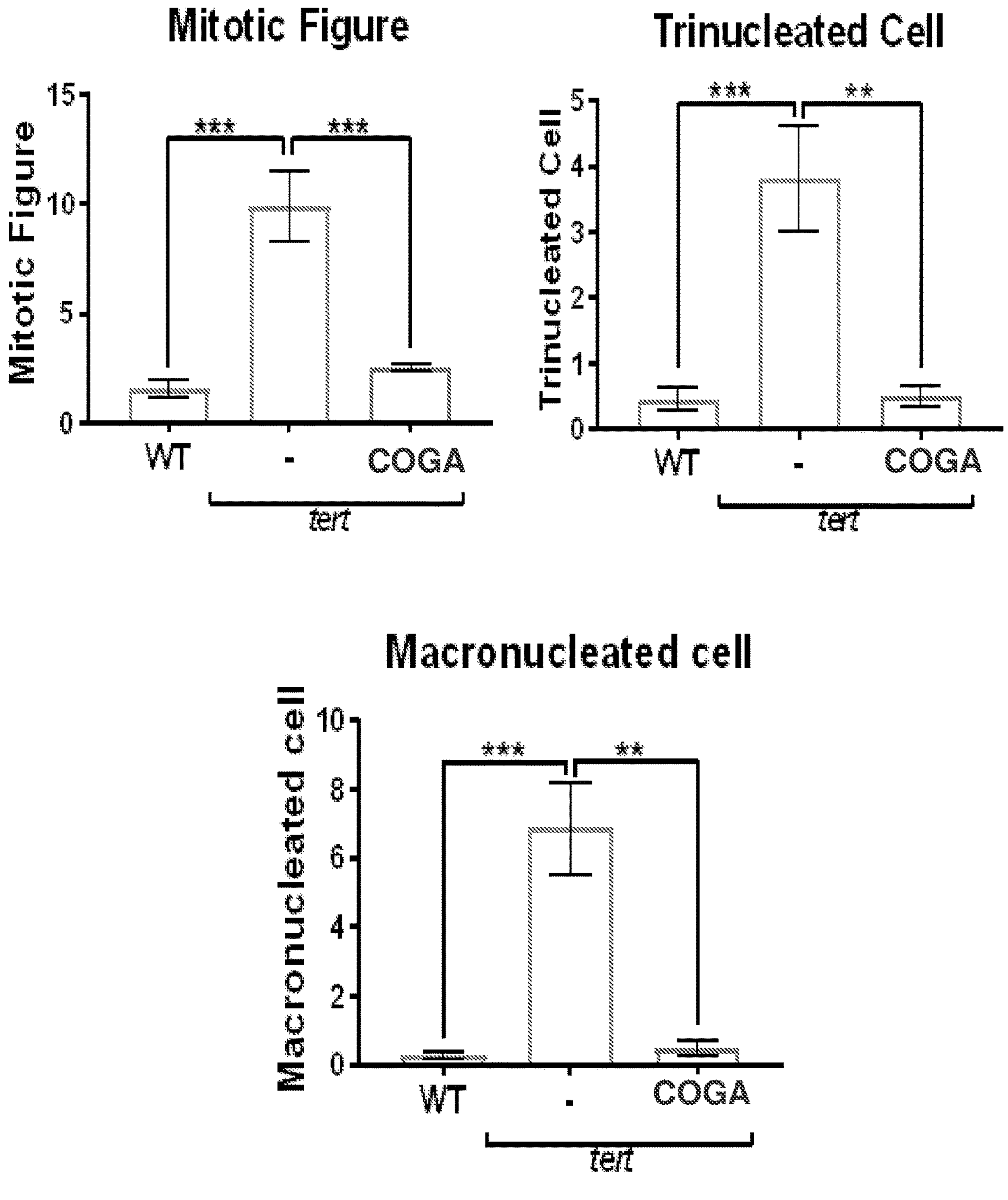
FIG. 6 shows that COGA treatment reduces the mitotic figures, trinucleated cells, and macronucleated cells in tert transgenic fish at 15 dpf.
Figure 8:
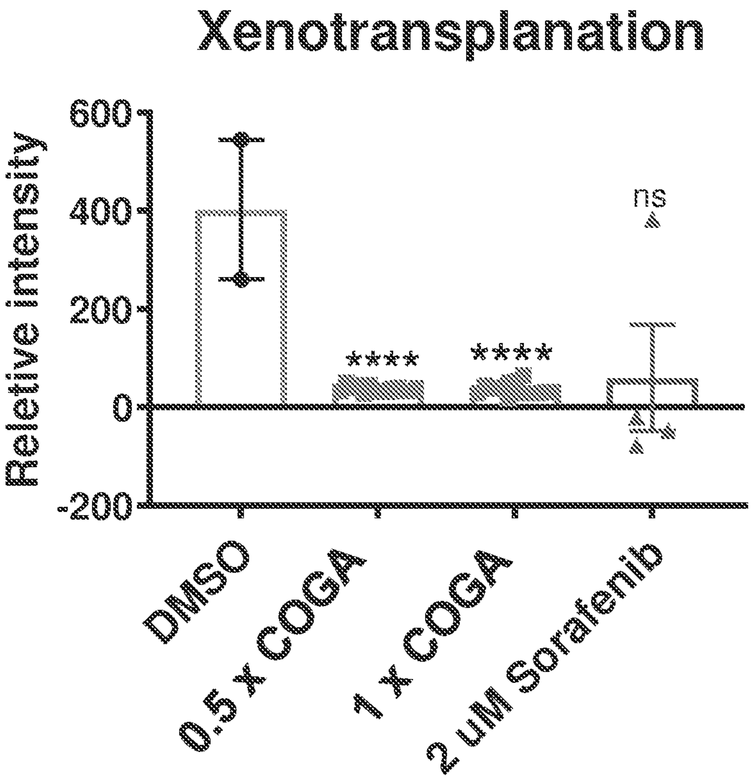
FIG. 8 shows that COGA treatment reduces hepatoma cell proliferation.

2.6 COGA Treatment Significantly Reduced the Mitotic Figures and Trinucleated Cells in Tert Zebrafish at 15 Dpf H&E staining is mainly to observe the states of mitotic figures, trinucleated cells, and macronucleated cells that represent hepatocyte undergoes carcinogenesis. FIG. 8 below shows the results of our analysis of hematoxylin-eosin (H&E) staining of zebrafish liver cells. As shown in FIG. 6, tert transgenic zebrafish has a high ratio of mitotic figures, trinucleated cells, and macronucleated cells compare to WT. Treated with COGA significantly reduced the number of mitotic figures, trinucleated cells, and macronucleated cells in tert transgenic zebrafish to those similar to WT zebrafish.

2.7 the COGA Treatment does not have Hepatotoxicity

Figure 7:
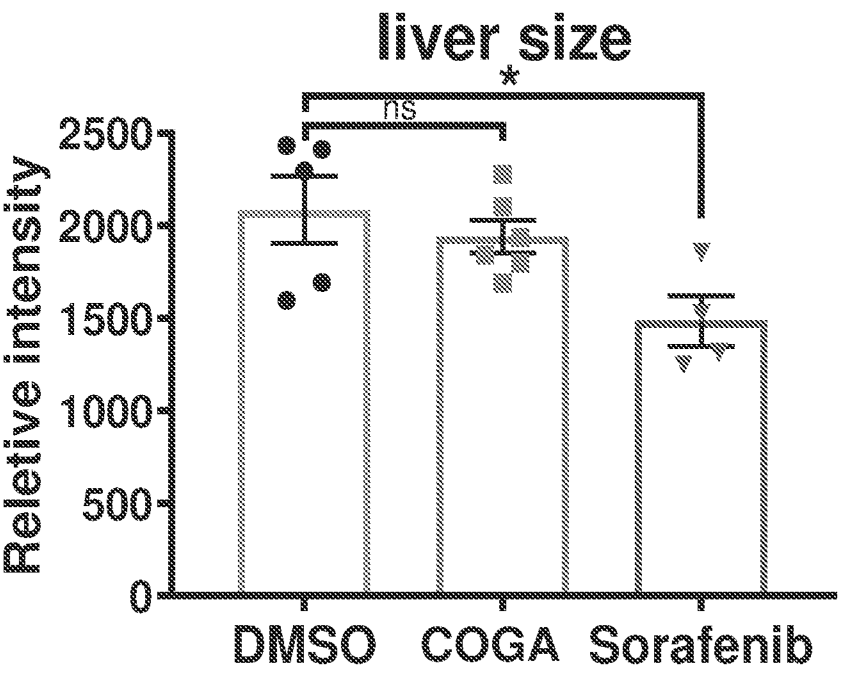
FIG. 7 shows that COGA treatment does not induce hepatotoxicity.

Gong's lab has developed an in-vivo hepatoxicity assay using zebrafish embryos[43]. To check whether the COGA possess toxicity to zebrafish liver, we used 3 dpf Tg(fabp10a:EGFP-mCherry) embryos which show green and red florescence in the liver as indicator, and treated with 1% DMSO, 1×(100 μM) COGA, and 10 μM Sorafenib separately. Images were analyzed by Image J software. We found that compared to DMSO treated control, Sorafenib significantly reduce liver size, suggested 10 μM of Sorafenib might be liver toxic (FIG. 7). However, we found the 100 μM COGA treatment has no liver toxicity as indicated by the liver size are similar to the DMSO control.

2.8 the COGA Reduced Cell Proliferation in Xenotransplantation Model

Using xenotransplantation, we injected Hep3B hepatoma cells to zebrafish embryos, and treated with COGA and Sorafenib for two days, and measured the cell proliferation changes after drug treatment (FIG. 8). We found both 0.5×(50 μM) COGA and 1×(100 μM) COGA significantly reduced hepatoma cell proliferation compared to the DMSO treatment.

2.9 the COGA Treatment Reduced Cell Proliferation in Various Cancer Cells

The results are shown in Table 1-3. The COGA treatment reduced A375, Huh7, and U-87 MG cell survival. The A375, Huh7, and U-87 MG cells treated with COGA showed $IC_{50}$ values of 68.7±15.8, 286.6±61.8, and higher than 10,000 nM, respectively

TABLE 1

| Data were shown for effects of COGA on survival of A375 cells. | | | | | | | | |
|---|---|---|---|---|---|---|---|---|
| | AMBG1 A375 cell survival (%) Conc. (nM) | | | | | | | |
| | 10000 | 3333 | 1111 | 370 | 123 | 41 | 14 | 5 |
| Replicate 1[a] | 88 | 76 | 71 | 68 | 69 | 71 | 87 | 104 |
| Replicate 2[a] | 84 | 72 | 67 | 62 | 67 | 68 | 85 | 105 |
| Replicate 3[a] | 89 | 77 | 70 | 69 | 72 | 74 | 89 | 110 |

[a]data were presented as percentage compared to control without drug treatment.

TABLE 2

| Data were shown for effects of COGA on survival of Huh7 cells. | | | | | | | | |
|---|---|---|---|---|---|---|---|---|
| | AMBG1 Huh7 cell survival (%) Conc. (nM) | | | | | | | |
| | 10000 | 3333 | 1111 | 370 | 123 | 41 | 14 | 5 |
| Replicate 1[a] | 92 | 82 | 79 | 75 | 77 | 80 | 92 | 107 |
| Replicate 2[a] | 82 | 75 | 73 | 69 | 71 | 72 | 84 | 100 |
| Replicate 3[a] | 89 | 80 | 82 | 74 | 73 | 78 | 88 | 102 |

[a]data were presented as percentage compared to control without drug treatment.

TABLE 3

| Data were shown for effects of COGA on survival of U-87 MG cells. | | | | | | | | |
|---|---|---|---|---|---|---|---|---|
| | AMBG1 U-87 MG cell survival (%) Conc. (nM) | | | | | | | |
| | 10000 | 3333 | 1111 | 370 | 123 | 41 | 14 | 5 |
| Replicate 1[a] | 88 | 84 | 84 | 85 | 89 | 89 | 95 | 103 |
| Replicate 2[a] | 89 | 87 | 87 | 87 | 89 | 89 | 95 | 100 |
| Replicate 3[a] | 90 | 89 | 90 | 91 | 89 | 93 | 97 | 105 |

[a]data were presented as percentage compared to control without drug treatment.

Figure 9:
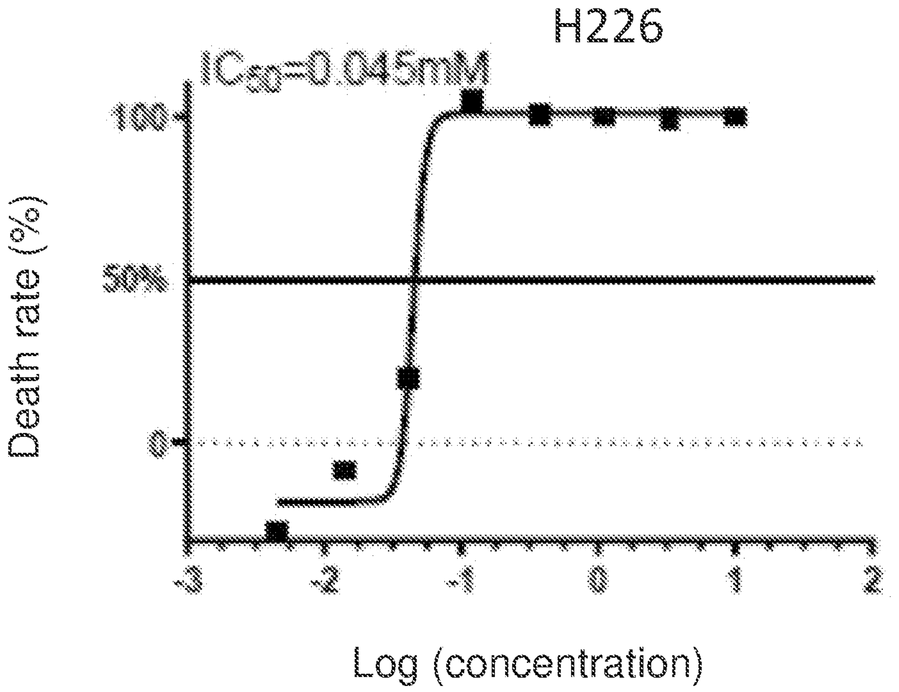
FIG. 9 shows the dose-response curve indicating inhibition of NCI-H226 cell proliferation by COGA at each experiment. The sigmoidal dose-response curves were generated by fitting the cell proliferation ratio as a function of logarithm of drug concentrations using GraphPad Prism with percentage inhibition value at each experiment.
Figure 9:
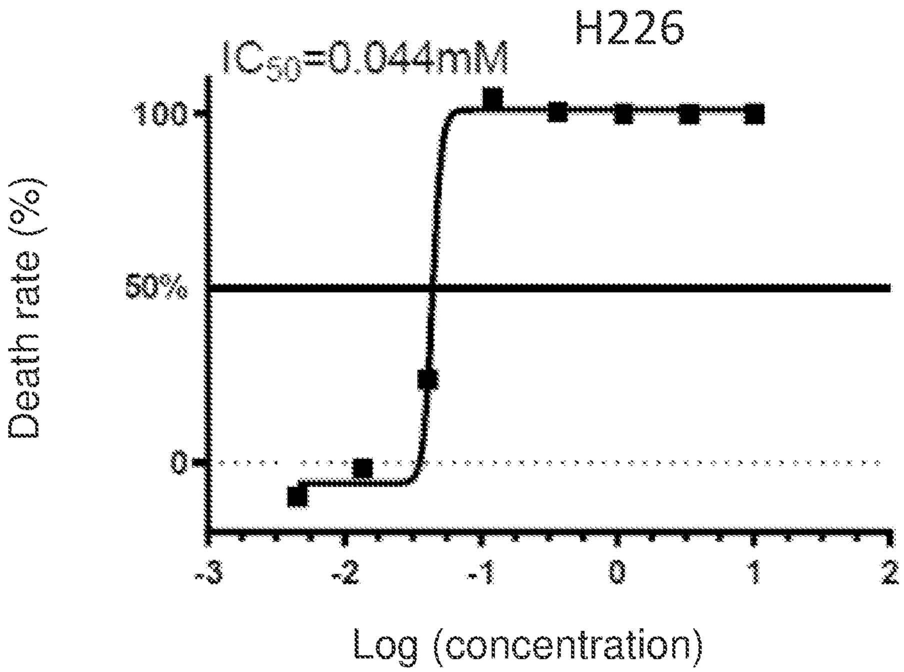

The anti-proliferation assay of COGA on NCI-H226 (lung carcinoma cells) was determined at 72 hours post-treatment using the MTS (Promega) colorimetric assay. The drug treatments were performed in triplicate wells and the experiment repeated two times. 50% inhibitory concentrations (IC50) of a tested compound were calculated using GraphPad Prism software. The dose-response curve of each experiment as shown in FIG. 9, demonstrating concentration dependent inhibition of NCI-H226 cell proliferation by COGA. The results indicate that COGA effectively inhibits NCI-H226 cell proliferation, with mean IC50 values of 0.045 mM.

TABLE 4

| Estimated $IC_{50}$ and mean $IC_{50}$ values of the drug treatment on A375, FaDu, HeLa, K-562, NCI-H226 and U87 cells. | |
|---|---|
| Cells | mean $IC_{50}$ values (mM) |
| A375 | 0.102 ± 0.002 |
| FaDu | 0.0746 ± 0.063 |
| HeLa | 0.0737 ± 0.0190 |
| K-562 | 0.0545 ± 0.0044 |

TABLE 4-continued

| Estimated $IC_{50}$ and mean $IC_{50}$ values of the drug treatment on A375, FaDu, HeLa, K-562, NCI-H226 and U87 cells. | |
|---|---|
| Cells | mean $IC_{50}$ values (mM) |
| NCI-H226 | 0.0445 ± 0.0007 |
| U87 | 0.042 ± 0.000 |

Estimated IC50 values were calculated based on non-linear regression of the dose-response curves of the cell proliferation ratio (%) as a function of logarithm of drug concentrations at each experiment.
Mean $IC_{50}$ data are expressed as mean ± SD values from two to three experiments.

The results indicate that COGA effectively inhibits A375, FaDu, HeLa, K-562, NCI-H226 and U87 cell proliferation.

3. CONCLUSIONS

Our experiment demonstrate that a cobalt-containing complex with an acidic acid amino e.g. COGA has no hepatoxicity and embryonic toxicity. The cobalt-containing complex exhibits strong anti-liver cancer effect in tert transgenic fish and xenotransplantation model. It also exhibits anti-proliferation activity in various cancer cells, including glioblastoma cells, melanoma cells, hepatocellular carcinoma cells, lung cancer cells, pharynx squamous carcinoma cells, cervical epithelioid carcinoma cells and leukemia cells.

We claim:

1. A method of treating cancer in a subject in need thereof comprising administering to the subject an effective amount of a cobalt-containing complex with an acidic amino acid, wherein the complex is a cobalt-containing glutamic acid (COGA) complex represented by Formula I Formula I

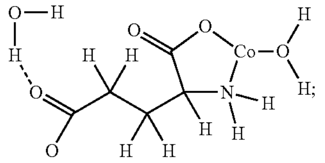

C5 H11 Co N O6 and/or the complex is a cobalt-containing aspartic acid (COAA) complex represented by Formula II Formula II

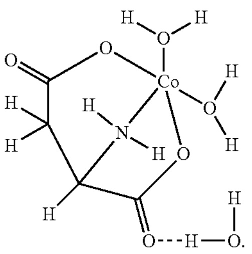

C4 H11 Co N O7

2. The method of claim 1, wherein the complex is the COGA complex of Formula I.

3. The method of claim 1, wherein the complex is the COAA complex of Formula II.

4. The method of claim 1, wherein the complex is in the form of crystals.

5. The method of claim 1, wherein the cancer is selected from the group consisting of liver cancer, brain cancer, skin cancer, lung cancer, head and neck cancer, breast cancer, cervical cancer, colon cancer, gastric cancer, leukemia, kidney cancer, ovarian cancer, pancreatic cancer, prostate cancer, and testicular cancer.

6. The method of claim 1, wherein the complex is administered in an amount effective in inhibiting proliferation of the cancer cells.

7. The method of claim 1, wherein the complex is administered in an amount effective in inhibiting expression of myca, mycb, cdk1, cdk2, ccnd1 and/or ccne1 in the cancer cells.

* * * * *